US011523802B2

(12) United States Patent
Vignon et al.

(10) Patent No.: US 11,523,802 B2
(45) Date of Patent: Dec. 13, 2022

(54) GRATING LOBE ARTEFACT MINIMIZATION FOR ULTRASOUND IMAGES AND ASSOCIATED DEVICES, SYSTEMS, AND METHODS

(71) Applicant: KONINKLIJKE PHILIPS N.V., Eindhoven (NL)

(72) Inventors: Francois Guy Gerard Marie Vignon, Andover (MA); David Hope Simpson, Bothell, WA (US); Andrew Hancock, Sacramento, CA (US); Seungsoo Kim, Andover, MA (US); Jun Seob Shin, Medford, MA (US); Jean-luc Francois-Marie Robert, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 271 days.

(21) Appl. No.: 16/708,977

(22) Filed: Dec. 10, 2019

(65) Prior Publication Data
US 2020/0187912 A1 Jun. 18, 2020

Related U.S. Application Data

(60) Provisional application No. 62/780,284, filed on Dec. 16, 2018.

(51) Int. Cl.
*A61B 8/00* (2006.01)
*A61B 8/08* (2006.01)
(Continued)

(52) U.S. Cl.
CPC .......... *A61B 8/5207* (2013.01); *A61B 8/0883* (2013.01); *A61B 8/12* (2013.01);
(Continued)

(58) Field of Classification Search
CPC ....... A61B 8/5207; A61B 8/0883; A61B 8/12; A61B 8/145; A61B 8/4488; A61B 8/461;
(Continued)

(56) References Cited

U.S. PATENT DOCUMENTS

| 6,776,763 | B2 | 8/2004 | Dickinson |
| 7,226,417 | B1 | 6/2007 | Eberle |

(Continued)

OTHER PUBLICATIONS

Johnson, Jeremy A. et al "Coherent-Array Imaging using Phased Subarrays. Part 1: Basic Principles", IEEE Transactions on Ultrasonics, Ferroelectrics, and Frequency Control, vol. 52, No. 1, Jan. 2005, pp. 37-50.

(Continued)

*Primary Examiner* — Keith M Raymond
*Assistant Examiner* — Adam D. Kolkin

(57) ABSTRACT

Ultrasound imaging system, devices, and methods for minimizing grating lobe artefacts in an ultrasound image are provided. For example, an ultrasound imaging system can include an array of acoustic elements and a processor in communication with the array. The processor controls the array to activate a plurality of apertures and subapertures in a scan sequence, generate an image comprising a plurality of pixels, identify at least one subaperture of the plurality of subapertures corresponding to a reduced signal value for one or more pixels of the image, and generate a grating-lobe-minimized image based on the identified subapertures. The grating-lobe-minimized image can be output to a display or combined with the original ultrasound image to include image features lost or reduced in the grating-lobe-minimized image. The grating-lobe-minimized image advantageously reduces image artefacts and clutter to simplify ultrasound image analysis and diagnosis procedures.

19 Claims, 12 Drawing Sheets

(51) Int. Cl.
*A61B 8/12* (2006.01)
*A61B 8/14* (2006.01)
*G06T 5/20* (2006.01)
*G06T 7/00* (2017.01)

(52) U.S. Cl.
CPC ............ *A61B 8/145* (2013.01); *A61B 8/4488* (2013.01); *A61B 8/461* (2013.01); *A61B 8/54* (2013.01); *G06T 5/20* (2013.01); *G06T 7/0012* (2013.01); *G06T 2207/10132* (2013.01); *G06T 2207/30021* (2013.01); *G06T 2207/30168* (2013.01)

(58) Field of Classification Search
CPC ........... A61B 8/54; G06T 5/20; G06T 7/0012; G06T 2207/10132; G06T 2207/30021; G06T 2207/30168
See application file for complete search history.

(56) References Cited

U.S. PATENT DOCUMENTS

| | | | |
|---|---|---|---|
| 7,846,101 B2 | 12/2010 | Eberle | |
| 2009/0141957 A1* | 6/2009 | Yen | G01S 15/8977 382/131 |
| 2014/0056099 A1* | 2/2014 | Hancock | A61B 8/12 367/11 |
| 2015/0305710 A1 | 10/2015 | Stigall | |
| 2016/0051233 A1* | 2/2016 | Mo | A61B 8/463 600/441 |
| 2016/0104267 A1 | 4/2016 | Hancock | |
| 2017/0301094 A1* | 10/2017 | Vignon | G06T 5/20 |

OTHER PUBLICATIONS

Samson, Christopher A. et al "Real-time, 45 MHz, Split-Aperture Phased Array Beamformer with Efficient Sign Coherence Grating Lobe Suppression", IEEE International Ultrasonics Symposium Proceedings, 2016.

* cited by examiner

FIG. 5

| TX | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| RX | | | | | | | | | | | | | | | |
| 1 | 1 | | | | | | | | | | | | | | |
| 2 | 2 | 28 | | | | | | | | | | | | | |
| 3 | 3 | 27 | 29 | | | | | | | | | | | | |
| 4 | 4 | 26 | 30 | 56 | | | | | | | | | | | |
| 5 | 5 | 25 | 31 | 55 | 57 | | | | | | | | | | |
| 6 | 6 | 24 | 32 | 54 | 58 | 84 | | | | | | | | | |
| 7 | 7 | 23 | 33 | 53 | 59 | 83 | 85 | | | | | | | | |
| 8 | 8 | 22 | 34 | 52 | 60 | 82 | 86 | 112 | | | | | | | |
| 9 | 9 | 21 | 35 | 51 | 61 | 81 | 87 | 111 | 113 | | | | | | |
| 10 | 10 | 20 | 36 | 50 | 62 | 80 | 88 | 110 | 114 | 140 | | | | | |
| 11 | 11 | 19 | 37 | 49 | 63 | 79 | 89 | 109 | 115 | 139 | 141 | | | | |
| 12 | 12 | 18 | 38 | 48 | 64 | 78 | 90 | 108 | 116 | 138 | 142 | 168 | | | |
| 13 | 13 | 17 | 39 | 47 | 65 | 77 | 91 | 107 | 117 | 137 | 143 | 167 | 169 | | |
| 14 | 14 | 16 | 40 | 46 | 66 | 76 | 92 | 106 | 118 | 136 | 144 | 166 | 170 | 196 | |
| 15 | | 15 | 41 | 45 | 67 | 75 | 93 | 105 | 119 | 135 | 145 | 165 | 171 | 195 | 197 |
| 16 | | | 42 | 44 | 68 | 74 | 94 | 104 | 120 | 134 | 146 | 164 | 172 | 194 | 198 |

FIG. 8

GRATING LOBE ARTEFACT MINIMIZATION FOR ULTRASOUND IMAGES AND ASSOCIATED DEVICES, SYSTEMS, AND METHODS

CROSS-REFERENCE TO PRIOR APPLICATIONS

This application claims the benefit of U.S. Provisional Application Ser. No. 62/780,284, filed Dec. 16, 2018 which is incorporated by reference herein.

TECHNICAL FIELD

The present disclosure relates generally to ultrasound imaging and, in particular, to generate grating-lobe-minimized ultrasound images. For example, an ultrasonic medical imaging device can include an array of acoustic elements configured to obtain ultrasound data, the array being in communication with a processor configured to process the obtained ultrasound data based on a plurality of subapertures generated with the array.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual acoustic elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

In IVUS imaging, a clinical goal is reducing ultrasound image artefacts, such as artefacts produced by grating lobes. Grating lobe artefacts, which appear as blurry, off-axis duplicates of on-axis objects, are particularly common in ultrasound images that are spatially-undersampled. Spatially-undersampled images can result from arrays that do not satisfy the Nyquist sampling criterion, which requires that the pitch, or spacing between acoustic elements in the array, be smaller than half the center wavelength. Given the frequencies at which IVUS imaging devices operate, it may be difficult to manufacture IVUS imaging arrays with acoustic elements and spacings that are small enough to satisfy the Nyquist criterion.

SUMMARY

Embodiments of the present disclosure provide improved ultrasound imaging devices and methods of operating the devices that minimize grating lobe artefacts in an ultrasound image. For example, an ultrasound imaging device can include an array of acoustic elements configured to emit ultrasound energy and receive echoes corresponding to the emitted ultrasound energy. A processor is configured to control the array according to a scan sequence to activate a plurality of apertures each comprising a plurality of subapertures. The processor analyzes pixels or groups of pixels in the generated image to identify which subaperture or subapertures produce a reduced or minimized signal value, and generates a grating-lobe-minimized image using the identified subapertures. The grating-lobe-minimized image can be output to a display or combined with the original ultrasound image to include image features lost or reduced in the grating-lobe-minimized image. The grating-lobe-minimized image advantageously reduces image artefacts and clutter to simplify ultrasound image analysis and diagnosis procedures.

In one aspect of the present disclosure, an ultrasound imaging system includes an array of acoustic elements configured to transmit ultrasound energy into an anatomy and to receive ultrasound echoes associated with the anatomy and a processor in communication with the array. The processor is configured to: control the array to activate a plurality of apertures in a scan sequence, each aperture of the plurality of apertures comprising a plurality of subapertures associated with one or more acoustic elements of the array; generate an image comprising a plurality of pixels, wherein each pixel is associated with signal values acquired by one or more subapertures of the plurality of subapertures; identify, for one or more pixels of the image, at least one subaperture of the plurality of subapertures corresponding to a reduced signal value for the one or more pixels; generate a minimized image based on the identified at least one subaperture for the one or more pixels; and output, to a display in communication with the processor, a grating lobe minimized image based on the image and the minimized image.

In some embodiments, the processor is configured to identify, for the one or more pixels of the image, a single subaperture of the plurality of subapertures corresponding to a minimum signal value for the one or more pixels. In some embodiments, the processor is further configured to generate a weighting mask based on the minimized image and the image, and apply the weighting mask to the image to generate a weighted image. According to some aspects, the image comprises a full aperture image, and the processor generating the weighting mask includes calculating a pixel-by-pixel ratio of a filtered minimized image and a filtered full aperture image. In other aspects, the filtered minimized image comprises at least one of a low-pass-filtered minimized image or a median-filtered minimized image, and the filtered full aperture image comprises at least one of a low-pass-filtered full aperture image or a median-filtered full aperture image. In still other embodiments, the processor is configured to generate the grating lobe minimized image, and the processor generating the grating lobe minimized image includes a log compression of the weighted image. In some embodiments, each aperture spans N transmit elements and N receive elements of the array, each subaperture spans M transmit elements and M receive elements of the array, and M is less than N. Each subaperture is associated with a contiguous portion of the acoustic elements of a corresponding aperture, in some embodiments. In still other aspects, the ultrasound imaging system comprises an intravascular ultrasound (IVUS) catheter, and the array is positioned around a distal portion of the IVUS catheter.

According to another embodiment of the present disclosure, a method for ultrasound imaging includes: activating, by a processor in communication with an array of acoustic elements, a plurality of apertures in a scan sequence, each aperture of the plurality of apertures associated with a scan line and comprising a plurality of subapertures associated with one or more acoustic elements of the array; generating an image comprising a plurality of scan lines that include signal values over a range of depths; comparing, at one or more depths of the range of depths, signal values corresponding to one or more subapertures; determining, based on the comparing, a reduced signal value for the one or more depths; generating a minimized image based on the determined reduced signal values; and outputting, to a display in communication with the processor, a grating lobe minimized image based on the image and the minimized image.

In some embodiments, determining the reduced signal value for the one or more depths comprises identifying a single subaperture, for each pixel, that corresponds to a minimum signal value. In some embodiments, the method further includes generating a weighting mask based on the minimized image and the image, and applying the weighting mask to the image to generate a weighted image. According to some aspects, generating the image comprises generating a full aperture image, and generating the weighting mask includes calculating a pixel-by-pixel ratio of a filtered minimized image and a filtered full aperture image. In some aspects, the filtered minimized image comprises at least one of a low-pass-filtered minimized image or a median-filtered minimized image, and the filtered full aperture image comprises at least one of a low-pass-filtered full aperture image or a median-filtered full aperture image. In some embodiments, the method further includes generating, by the processor, the grating lobe minimized image by a log compression of the weighted image. In some embodiments, each aperture spans N transmit elements and N receive elements of the array, each subaperture spans M transmit elements and M receive elements of the array, and M is less than N. Each subaperture is associated with a contiguous portion of the acoustic elements of a corresponding aperture, in some embodiments. In still other embodiments, activating the plurality of apertures of the array comprises activating a plurality of apertures of an array positioned around a distal portion of an intravascular ultrasound (IVUS) catheter.

In another embodiment of the present disclosure, an ultrasound imaging system includes an array of acoustic elements configured to transmit ultrasound energy into an anatomy and to receive ultrasound echoes associated with the anatomy, and a processor in communication with the array. The processor is configured to: activate a plurality of apertures in a scan sequence, each aperture of the plurality of apertures comprising a plurality of subapertures associated with one or more acoustic elements of the array; generate an image comprising a plurality of pixels, wherein each pixel is associated with signal values acquired by one or more subapertures of the plurality of subapertures; generate a reduced image comprising a plurality of reduced signal pixels, wherein generating the plurality of reduced signal pixels comprises: comparing signal values corresponding to one or more subapertures associated with a corresponding pixel or group of pixels; and identifying, based on the comparing, a reduced signal value for the pixel or group of pixels; and output, to a display in communication with the processor, a grating lobe minimized image based on the image and the reduced image.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 5 is a diagrammatic graphical view of an ultrasound pulse sequence, according to aspects of the present disclosure.

FIG. 8 is a diagrammatic graphical view of an aperture of an ultrasound pulse sequence that includes a plurality of subapertures, according to aspects of the present disclosure.

DETAILED DESCRIPTION

Figure 1:
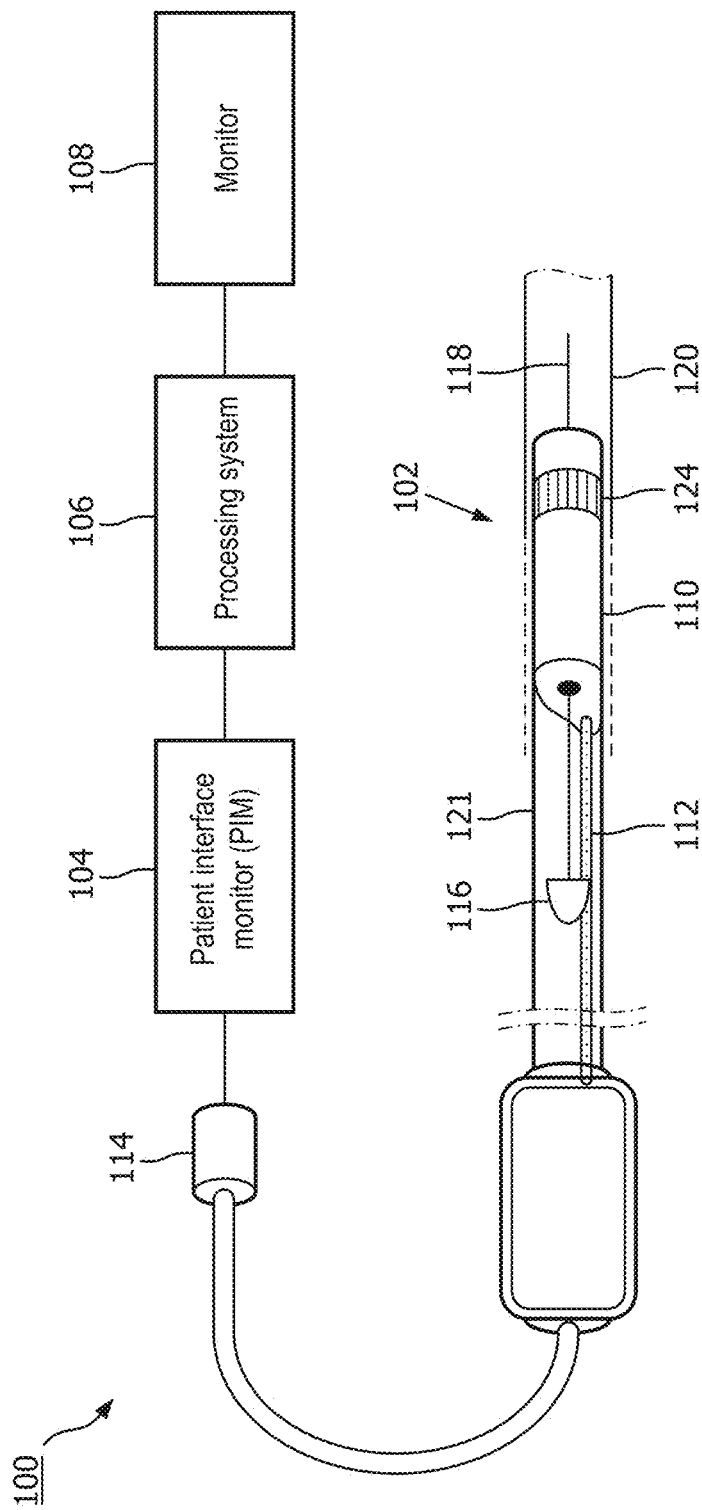
FIG. 1 is a diagrammatic schematic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound imaging system 100, according to aspects of the present disclosure. The ultrasound imaging system 100 can be an intraluminal imaging system. In some instances, the system 100 can be an intravascular ultrasound (IVUS) imaging system. The system 100 may include an intraluminal imaging device 102 such as a catheter, guide wire, or guide catheter, a patient interface module (PIM) 104, a processing system or console 106, and a monitor 108. The intraluminal imaging device 102 can be an ultrasound imaging device. In some instances, the device 102 can be IVUS imaging device, such as a solid-state IVUS device.

At a high level, the IVUS device 102 emits ultrasonic energy, or ultrasound signals, from a transducer array 124 included in scanner assembly 110 mounted near a distal end of the catheter device. The ultrasonic energy is reflected by tissue structures in the medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s), or acoustic element(s), to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 126 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

Figure 2:
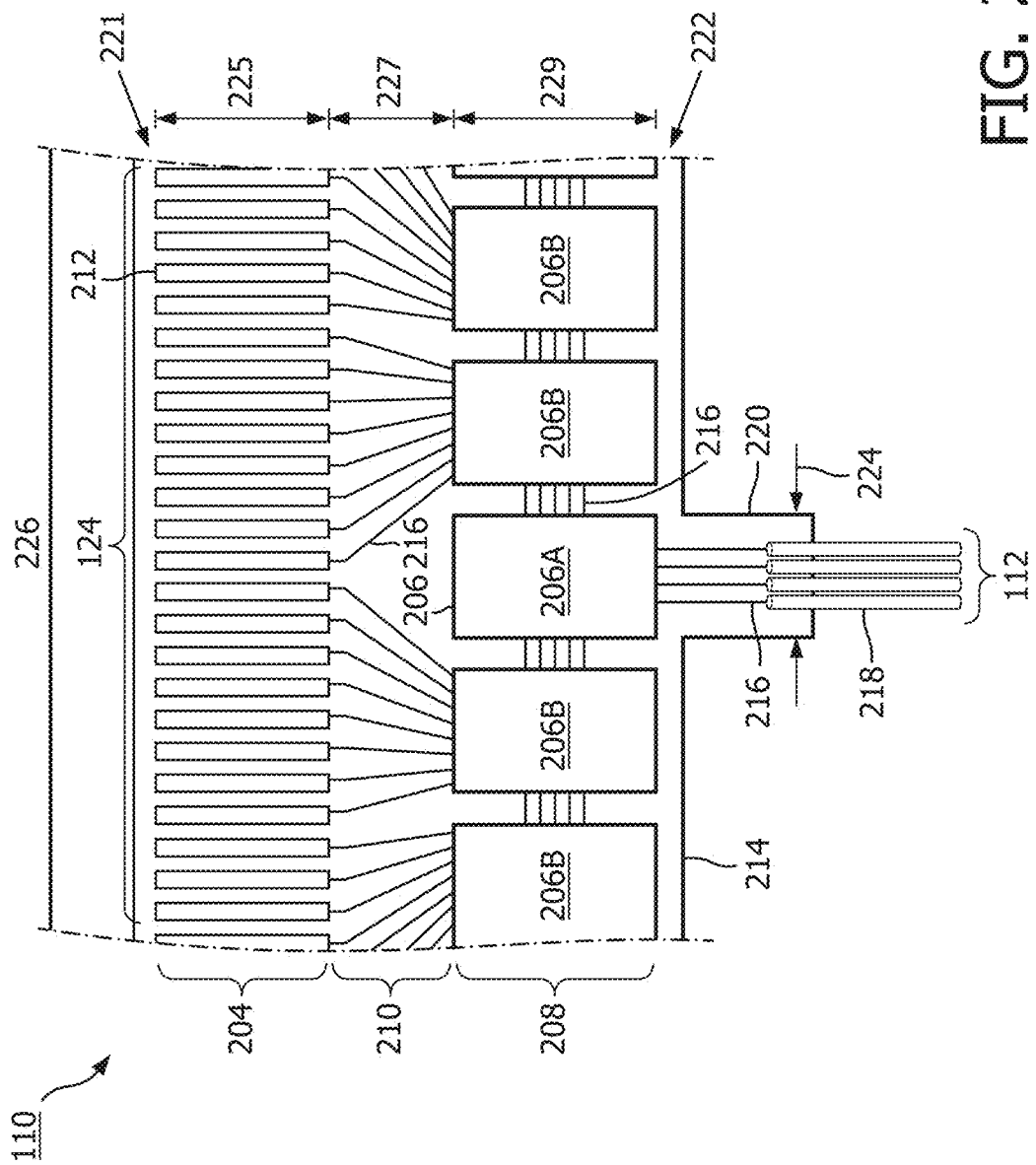
FIG. 2 is a diagrammatic view of the top of a scanner assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

In an embodiment, the image processing system 106 generates flow data by processing the echo signals from the IVUS device 102 into Doppler power or velocity information. The image processing system 106 may also generate B-mode data by applying envelope detection and logarithmic compression on the conditioned echo signals. The processing system 106 can further generate images in various views, such as 2D and/or 3D views, based on the flow data or the B-mode data. The processing system 106 can also perform various analyses and/or assessments. For example, the processing system 106 can apply virtual histology (VH) techniques, for example, to analyze or assess plaques within a vessel (e.g., the vessel 120). The images can be generated to display a reconstructed color-coded tissue map of plaque composition superimposed on a cross-sectional view of the vessel.

In an embodiment, the processing system 106 can apply a blood flow detection algorithm (e.g., ChromaFlo) to determine the movement of blood flow, for example, by acquiring image data of a target region (e.g., the vessel 120) repeatedly and determining the movement of the blood flow from the image data. The blood flow detection algorithm operates based on the principle that signals measured from vascular tissue are relatively static from acquisition to acquisition, whereas signals measured from blood flow vary at a characteristic rate corresponding to the flow rate. As such, the blood flow detection algorithm may determine movements of blood flow based on variations in signals measured from the target region between repeated acquisitions. To acquire the image data repeatedly, the processing system 106 may control to the device 102 to transmit repeated pulses on the same aperture.

While the present disclosure refers to intravascular ultrasound (IVUS) imaging using an intravascular catheter or guidewire, it is understood that one or more aspects of the present disclosure can be implemented in any suitable ultrasound imaging system, including a synthetic aperture ultrasound imaging system, a phased array ultrasound imaging system, or any other array-based ultrasound imaging system. For example, aspects of the present disclosure can be implemented in intraluminal ultrasound imaging systems using an intracardiac (ICE) echocardiography catheter and/or a transesophageal echocardiography (TEE) probe, and/or external ultrasound imaging system using an ultrasound probe configured for imaging while positioned adjacent to and/or in contact with the patient's skin. The ultrasound imaging device can be a transthoracic echocardiography (TTE) imaging device in some embodiments.

An ultrasound transducer array of ultrasound imaging device includes an array of acoustic elements configured to emit ultrasound energy and receive echoes corresponding to the emitted ultrasound energy. In some instances, the array may include any number of ultrasound transducer elements. For example, the array can include between 2 acoustic elements and 10000 acoustic elements, including values such as 2 acoustic elements, 4 acoustic elements, acoustic elements, 64 acoustic elements, 128 acoustic elements, 500 acoustic elements, 812 acoustic elements, 3000 acoustic elements, 9000 acoustic elements, and/or other values both larger and smaller. In some instances, the transducer elements of the array may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., one or more rows, one or more columns, and/or one or more orientations) can be uniformly or independently controlled and activated. The array can be configured to obtain one-dimensional, two-dimensional, and/or three-dimensional images of patient anatomy.

The ultrasound transducer elements may comprise piezoelectric/piezoresistive elements, piezoelectric micromachined ultrasound transducer (PMUT) elements, capacitive micromachined ultrasound transducer (CMUT) elements, and/or any other suitable type of ultrasound transducer elements. The ultrasound transducer elements of the array are in communication with (e.g., electrically coupled to) electronic circuitry. For example, the electronic circuitry can include one or more transducer control logic dies. The electronic circuitry can include one or more integrated circuits (IC), such as application specific integrated circuits (ASICs). In some embodiments, one or more of the ICs can comprise a microbeamformer (μBF). In other embodiments, one or more of the ICs comprises a multiplexer circuit (MUX).

FIG. 2 is a diagrammatic top view of a portion of a flexible assembly 200, according to aspects of the present disclosure. The flexible assembly 200 includes a transducer array 124 formed in a transducer region 204 and transducer control logic dies 206 (including dies 206A and 206B) formed in a control region 208, with a transition region 210 disposed therebetween.

The transducer control logic dies 206 are mounted on a flexible substrate 214 into which the transducers 212 have been previously integrated. The flexible substrate 214 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled flexible assembly 110. In some embodiments, the film layer is between 5 μm and 100 μm, with some particular embodiments being between 5 μm and 25.1 μm, e.g., 6 μm.

The transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or, the length 227 of the transition region 210 may be less than lengths 225 and 229, the length 227 of the transition region 210 can be greater than lengths 225, 229 of the transducer region and controller region, respectively.

The control logic dies 206 are not necessarily homogenous. In some embodiments, a single controller is designated a master control logic die 206A and contains the communication interface for cable 142 which may serve as an electrical conductor, e.g., electrical conductor 112, between a processing system, e.g., processing system 106, and the flexible assembly 200. Accordingly, the master control circuit may include control logic that decodes control signals received over the cable 142, transmits control responses over the cable 142, amplifies echo signals, and/or transmits the echo signals over the cable 142. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducers 212, in an embodiment, the flexible substrate 214 includes conductive traces 216 formed in the film layer that carry signals between the control logic dies 206 and the transducers 212. In particular, the conductive traces 216 providing communication between the control logic dies 206 and the transducers 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 142 when the conductors 218 of the cable 142 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 µm. For example, in an embodiment, 5 µm conductive traces 216 are separated by 5 µm of space. The width of a conductive trace 216 on the flexible substrate may be further determined by the width of the conductor 218 to be coupled to the trace/pad.

The flexible substrate 214 can include a conductor interface 220 in some embodiments. The conductor interface 220 can be a location of the flexible substrate 214 where the conductors 218 of the cable 142 are coupled to the flexible substrate 214. For example, the bare conductors of the cable 142 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, Liquid Crystal Polymer (LCP), and/or other suitable materials.

Figure 3:
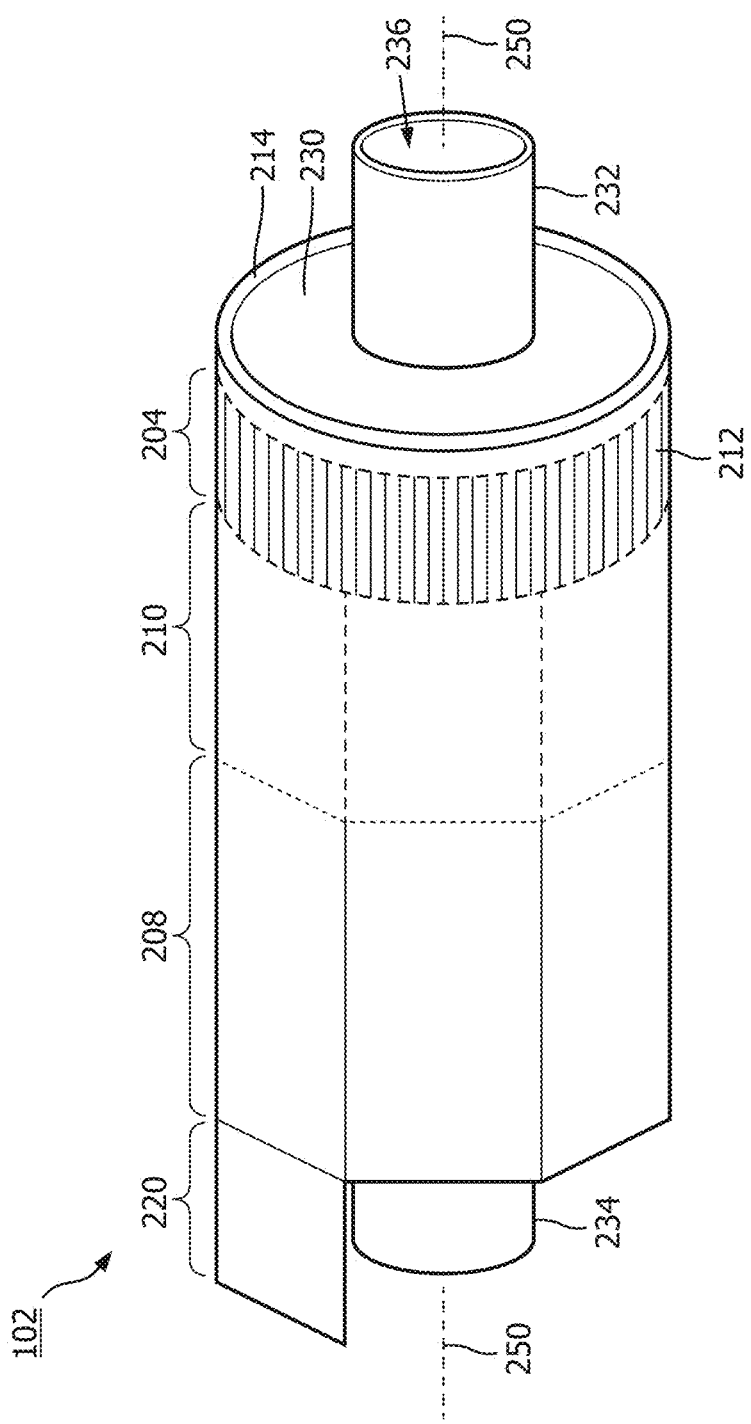
FIG. 3 is a diagrammatic perspective view of the scanner assembly shown in FIG. 2 in a rolled configuration around a support member, according to aspects of the present disclosure.

FIG. 3 illustrates a perspective view of the device 102 with the scanner assembly 110 in a rolled configuration. In some instances, the assembly 110 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety.

In some embodiments, the transducer elements 212 and/or the controllers 206 can be positioned in in an annular configuration, such as a circular configuration or in a polygon configuration, around a longitudinal axis 250 of a support member 230. It will be understood that the longitudinal axis 250 of the support member 230 may also be referred to as the longitudinal axis of the scanner assembly 110, the flexible elongate member 121, and/or the device 102. For example, a cross-sectional profile of the imaging assembly 110 at the transducer elements 212 and/or the controllers 206 can be a circle or a polygon. Any suitable annular polygon shape can be implemented, such as a based on the number of controllers/transducers, flexibility of the controllers/transducers, etc., including a pentagon, hexagon, heptagon, octagon, nonagon, decagon, etc. In some examples, the plurality of transducer controllers 206 may be used for controlling the plurality of ultrasound transducer elements 212 to obtain imaging data associated with the vessel 120.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, ('220 Application) the entirety of which is hereby incorporated by reference herein. The support member 230 can be a ferrule having a distal flange or portion 232 and a proximal flange or portion 234. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined and/or electrochemically machined or laser milled, such as by removing material from a blank to shape the support member 230, or molded, such as by an injection molding process.

Figure 4:
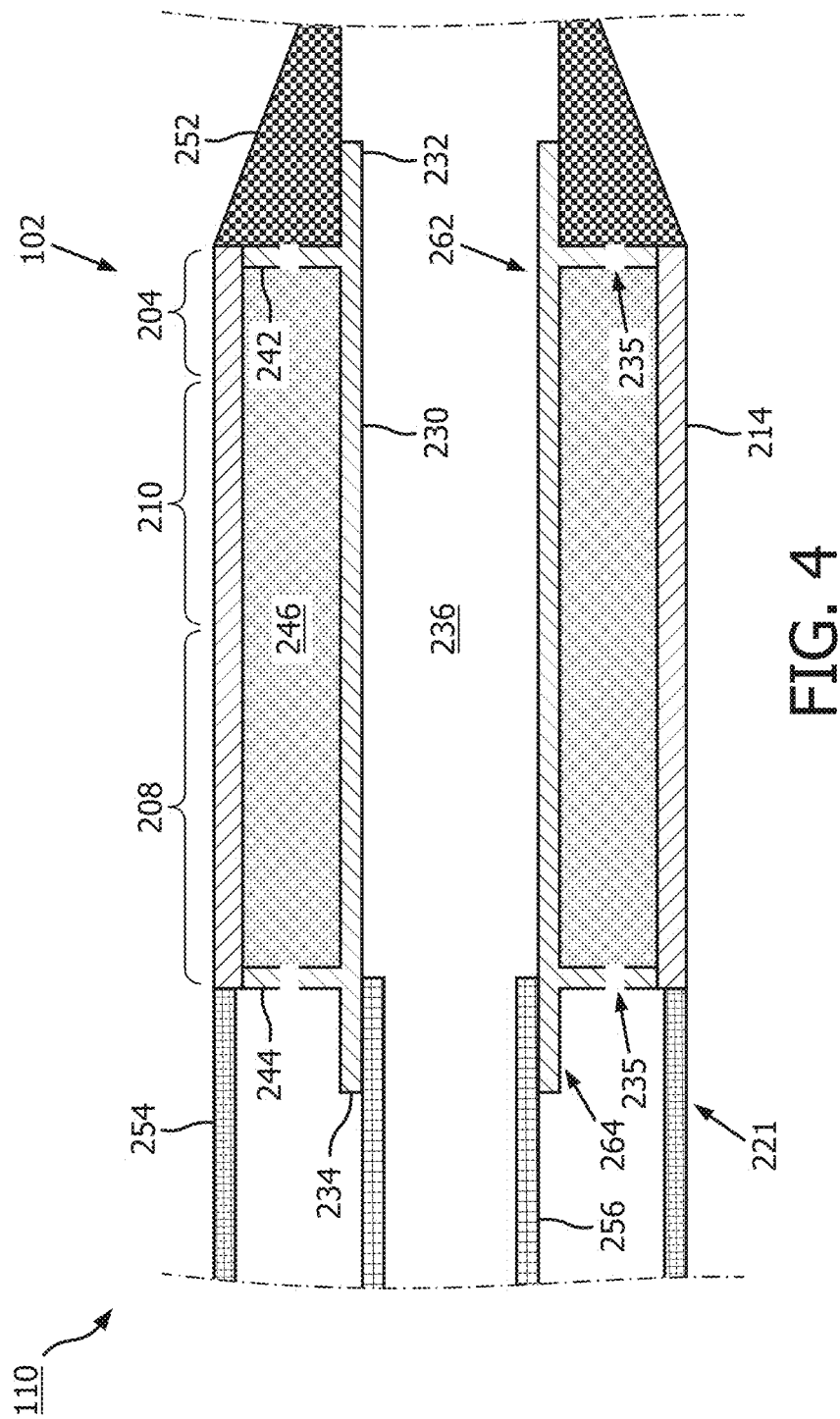
FIG. 4 is a diagrammatic cross-sectional side view of a scanner assembly in a rolled configuration around a support member, according to aspects of the present disclosure.

Referring now to FIG. 4, shown there is a diagrammatic cross-sectional side view of a distal portion of the intraluminal imaging device 102, including the flexible substrate 214 and the support member 230, according to aspects of the present disclosure. The support member 230 can be referenced as a unibody in some instances. The support member 230 can be composed of a metallic material, such as stainless steel, or non-metallic material, such as a plastic or polymer as described in U.S. Provisional Application No. 61/985, 220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending along the longitudinal axis LA. The lumen 236 is in communication with the entry/exit port 116 and is sized and shaped to receive the guide wire 118 (FIG. 1). The support member 230 can be manufactured according to any suitable process. For example, the support member 230 can be machined and/or electrochemically machined or laser milled, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 244 that extend vertically are provided at the distal and proximal portions 262, 264, respectively, of the support member 230. The stands 242, 244 elevate and support the distal and proximal portions of the flexible substrate 214. In that regard, portions of the flexible substrate 214, such as the transducer portion 204 (or transducer region 204), can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244 and can also have special features for rotational alignment as well as control chip placement and connection. To improve acoustic performance, any cavities between the flexible substrate 214 and the surface of the support member 230 are filled with a backing material 246. The liquid backing material 246 can be introduced between the flexible substrate 214 and the support member 230 via passageways 235 in the stands 242, 244. In some embodiments, suction can be applied via the passageways 235 of one of the stands 242, 244, while the liquid backing material 246 is fed between the flexible substrate 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. As the term is used herein, the shape of the support member 230 may reference a cross-sectional profile of the support member 230. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can comprise a flexible elongate member. The proximal inner member 256 can be received within a proximal flange 234. The proximal outer member 254 abuts and is in contact with the flexible substrate 214. A distal member 252 is coupled to the distal portion 262 of the support member 230. For example, the distal member 252 is positioned around the distal flange 232. The distal member 252 can abut and be in contact with the flexible substrate 214 and the stand 242. The distal member 252 can be the distal-most component of the intraluminal imaging device 102.

One or more adhesives can be disposed between various components at the distal portion of the intraluminal imaging device 102. For example, one or more of the flexible substrate 214, the support member 230, the distal member 252, the proximal inner member 256, and/or the proximal outer member 254 can be coupled to one another via an adhesive.

Figure 5:
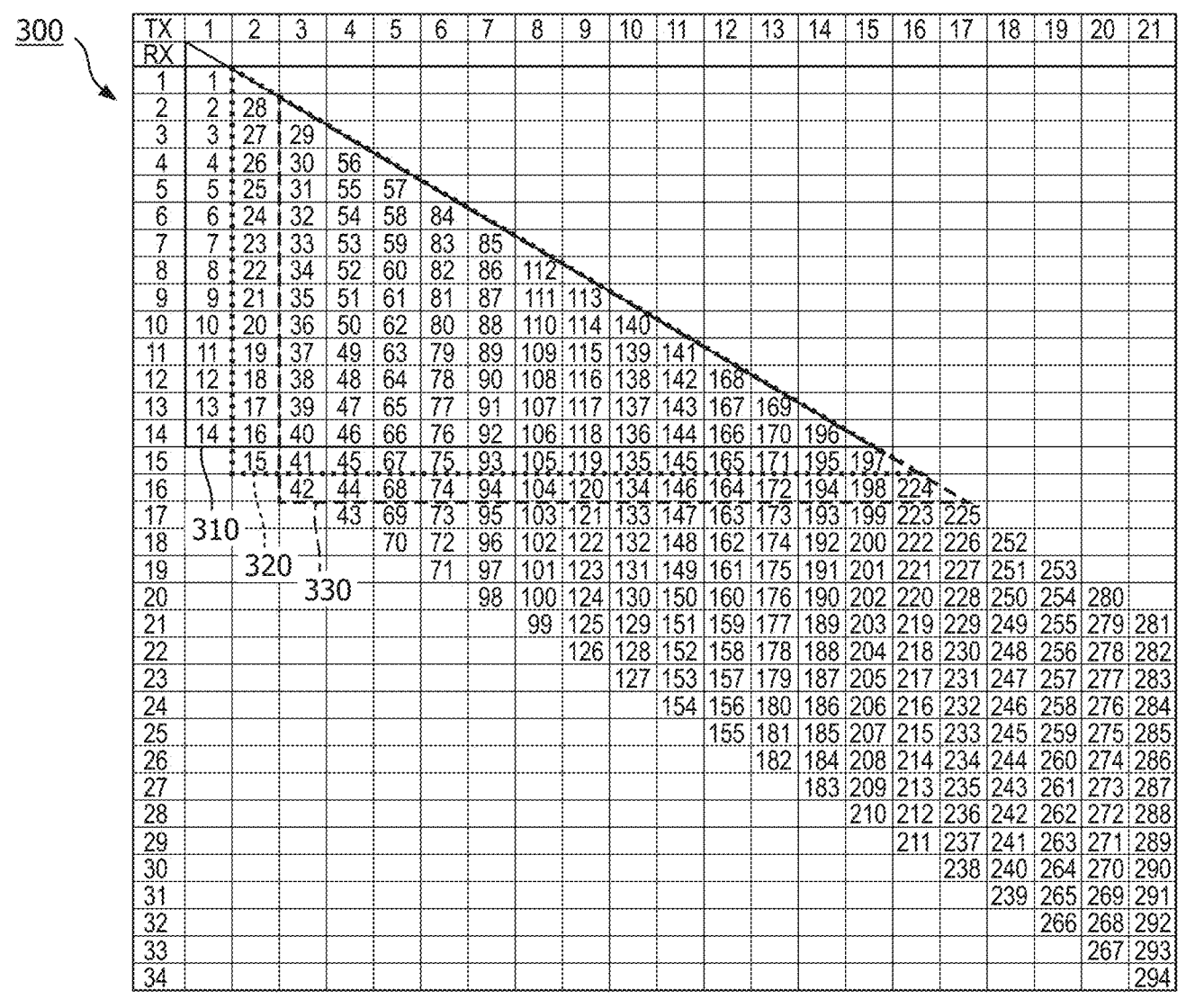

FIG. 5 is a diagrammatic graphical view showing an ultrasound pulse sequence of a solid-state IVUS device. The pulse sequence 300 comprises a contiguous "zig-zag" pattern or arrangement of transmit-receive pairs, which can alternatively be described as transmit-receive events. Each transmit-receive pair is represented by an index, or number, corresponding to a sequential time at which the corresponding transmit-receive pair is activated to obtain ultrasound imaging data. In that regard, each transmit-receive index is an integer representing its relative temporal position in the sequence 300. In the embodiment of FIG. 5, each transmit-receive index corresponds to a single transmit-receive pair. Each transmit-receive pair is defined by a transmit element index, shown on the x-axis, and a receive element index, shown on the y-axis. Each transmit element index and receive element index corresponds to an ultrasound element of an array of ultrasound transducer elements. In the embodiment shown in FIG. 5, the array comprises 64 ultrasound transducer elements.

For example, the transmit-receive pair associated with transmit-receive index "1" is defined by transmit element index number 1 and receive element index 1. In some embodiments, the transmit element index and receive element index correspond to the same ultrasound transducer element. In other embodiments, the transmit element index and receive element index correspond to different ultrasound transducer elements. For example, the transmit-receive pair numbered "2," which is shown directly below transmit-receive pair 1, is defined by transmit element index 1 and receive element index 2. That is, the ultrasound imaging data associated with transmit-receive pair 2 is obtained by activating transmit element index 1 to transmit ultrasound energy into the patient volume, and then activating receive element index 2 to receive ultrasound echoes from the patient volume. In FIG. 5, 294 transmit-receive pairs of an ultrasound pulse sequence are shown. Each transmit-receive pair is activated sequentially according to its transmit-receive index.

In the sequence 300, the ultrasound transducer element associated with transmit index 1 transmits 14 consecutive times, while the elements associated with receive indices 1 through 14 are sequentially activated to receive the corresponding echoes. Next, the element associated with transmit index 2 transmits 14 consecutive times, while the elements associated with receive indices 15 through 2 (stepping backward) are sequentially activated to receive the corresponding echoes. This sequence continues in a zig-zag pattern around the array of ultrasound transducer elements. Each transmit-receive pair is associated with one or more apertures 310, 320, 330. For example, a first aperture 310 comprises transmit-receive pairs spanning from index 1 to index 196, a second aperture 320 comprises transmit-receive pairs spanning from index 15 to index 197, and a third aperture 330 comprises transmit-receive pairs spanning from index 29 to index 224. The transmit-receive pairs in each aperture are combined to form an A-line for a B-mode image. Thus, the transmit-receive pairs contained within the first aperture 310 are combined to form a first A-line, the transmit-receive pairs contained within the second aperture 320 are combined to form a second A-line, the transmit-receive pairs contained within the third aperture are combined to form a third A-line, and so on. The A-line formed by the first aperture 310 will be centered between transmit and receive element indices 7 and 8, the A-line formed by the second aperture 320 will be centered between transmit and receive element indices numbered 8 and 9, the A-line formed by the third aperture 330 will be centered between transmit and receive element indices numbered 9 and 10, and so on. Several apertures are used to form A-lines, which are combined and arranged to form a B-mode image.

It will be understood that, to complete the sequence 300 shown in FIG. 5 for an ultrasound transducer array comprising 64 elements, 64 apertures comprising a total of 896 transmit-receive pairs are used to form a single B-mode image frame. However, if pulse averaging is used to increase signal-to-noise ratio, at least twice as many transmit-receive pairs (1792) are required. At a pulse repetition frequency of 50 kHz, 1792 transmit-receive pairs corresponds to a 30 Hz frame rate, which is near the minimum acceptable frame rate for real-time imaging, and may already limit the ability to do pullbacks with an IVUS imaging device.

Grating lobe artefacts can appear in an image due to one or more off-axis objects reflecting an unfocused portion (e.g., a grating lobe) of an ultrasound pulse back to the acoustic elements of the array. Ultrasound transducer arrays that do not satisfy the Nyquist criteria may be particularly susceptible to producing grating lobe artefacts. Grating lobe artefacts appear in B-mode ultrasound images as blurry duplicates of the off-axis target. Grating lobe artefacts add unwanted image clutter that complicates the image analysis process and makes it difficult for the physician or ultrasound technician to interpret ultrasound images, such as the tissue structure of a blood vessel.

Figure 6:
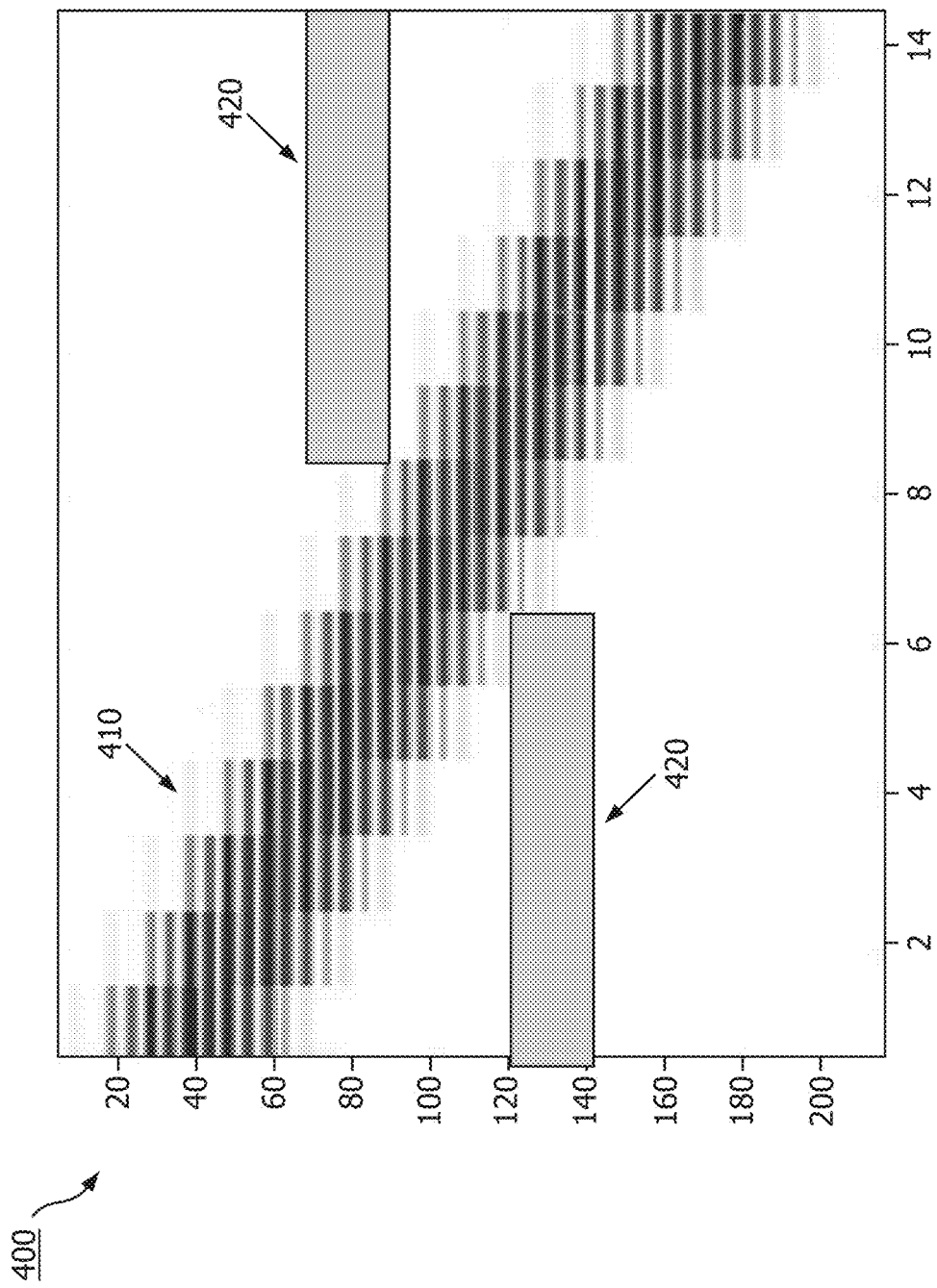
FIG. 6 is a diagrammatic graphical view of a channel domain response of an off-axis target in an aperture of an ultrasound pulse sequence, according to aspects of the present disclosure.

FIG. 6 is a graphical illustration of a channel domain 400 showing a signal response 410 associated with a grating lobe artefact. The y-axis represents fast-time, which corresponds to the time-of-flight of the ultrasound signals, or the spatial depth represented by the signal. The x-axis represents a plurality of acoustic elements (numbered 1 to 14) corresponding to an aperture of a scan sequence. Image signal 410 shows the signal response corresponding to a grating lobe artefact created by an off-axis target, with darker shades indicating stronger signals. The image signal 410 is tilted across the aperture channel domain, due to the fact that the target that creates the grating lobe artefact is off of the main beam axis. By contrast, on-axis targets within the main beam would appear as horizontal lines or rectangles across the channel domain graph 400. Due to the tilted nature of the grating lobe artefact in the channel domain 400, there exists at least one subaperture, or group of transmit-receive pairs, at any given depth that is substantially free of grating lobe artefacts. As shown in FIG. 6, at the depths corresponding to fast-times 80 and 130, each of which relates to a particular depth in an ultrasound image, the subapertures 420 comprised of elements 9 to 14, and 1 to 6, respectively, are substantially free of grating lobe artefact signals. Based on this characteristic of grating lobe artefact signals, subapertures can be chosen at each depth in a manner that minimizes the effects of grating lobes in an ultrasound image. In that regard, FIGS. 7-10 illustrate a method 500 for creating a grating lobe minimized image that includes identifying, for one or more pixels or depths, a subaperture that produces a reduced or minimized signal response. In some embodiments, such as the embodiment illustrated in FIGS. 7-10, the minimized signal value can include a minimum signal value of the signal values produced by different subapertures for a pixel or group of pixels. As explained further below, in other embodiments, the minimized signal value can include one or more signal values that are at or below a threshold signal value.

Figure 7:
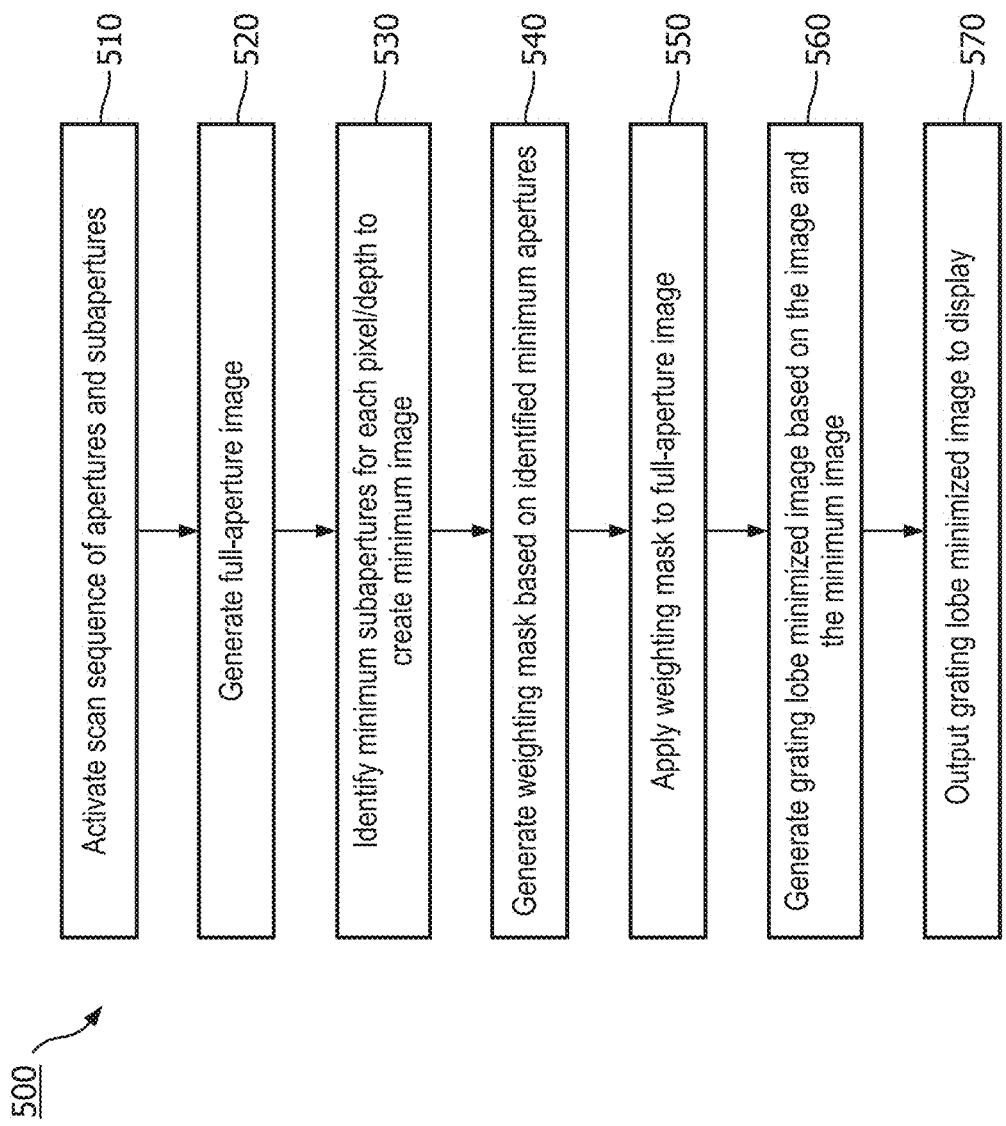
FIG. 7 is a flow diagram illustrating a method for minimizing grating lobe artefacts in an ultrasound image, according to aspects of the present disclosure.

FIG. 7 is a flow diagram illustrating a method 500 for generating a grating lobe minimized image. In step 510, a processor or processing system, such as the processing system 106 of FIG. 1, controls an array of acoustic elements of an ultrasound imaging device to activate a scan sequence that includes a plurality of apertures and subapertures. In some embodiments, the array of acoustic elements may be associated with an IVUS imaging device (e.g., 102, FIG. 1), where the array is positioned around a perimeter or circumference of a distal portion of the IVUS imaging device. In some embodiments, the scan sequence may be similar or identical to the scan sequence 300 shown in FIG. 5. For example, the scan sequence can include a pattern or sequence of transmit-receive pairs that can be arranged into apertures, where each aperture is used to form a single A-line of an ultrasound image. Furthermore, each aperture can include a plurality of subapertures corresponding to a sub-group of the transmit-receive pairs contained within the aperture. FIG. 8 illustrates the aperture 310 shown in FIG. 5, and a plurality of subapertures 312, 314, 316 contained within the aperture 310. Each subaperture comprises a contiguous sub-group of the transmit-receive pairs of the aperture 310. The subapertures 312, 314, 316 can exhibit triangular shapes in the scan sequence diagram, similar to the aperture 310. However, it will be understood that one or more subapertures can be arranged into or defined by other shapes or patterns, such as rectangles and/or polygons. In some embodiments, one or more subapertures can include a non-contiguous sub-group of transmit-receive pairs.

In the embodiment of FIG. 8, each subaperture 312, 314, 316 spans seven transmit elements, and seven receive elements, such that the aperture 310 can include as many as 28 subapertures, for example. In other embodiments, each subaperture can span fewer or more transmit and/or receive elements, such as 2, 3, 4, 5, 6, 8, 9, 10, or 12 elements. Similarly, in other embodiments, each aperture can span fewer or more elements, such as 6, 8, 10, 12, 16, 18, 20, or any other suitable number of elements.

Referring again to FIG. 7, in step 520, the processor generates a full-aperture image based on the received ultrasound data from the array. For example, in some embodiments, the image may be a B-mode ultrasound image comprising a plurality of A-line scans. Each pixel of the B-mode image is associated with a particular depth and a particular A-line scan. Each A-line scan is associated with a different aperture of a scan sequence, where each aperture spans a plurality of transmit and receive elements of the array. As explained above, in some aspects, the full-aperture image may include one or more grating lobe artefacts. Grating lobe artefacts can be particularly common for ultrasound probes with spatially under-sampled arrays, such as the arrays of IVUS imaging catheters.

In step 530, the processing system identifies, for one or more pixels in the B-mode image, at least one subaperture corresponding to a reduced or minimized signal response. In some embodiments, the processing system identifies one or more subapertures for each individual pixel. In other embodiments, the processing system identifies one or more subapertures for a group of pixels. In some embodiments, the processing system can identify subapertures using image kernels of size M×N, where M and N can each range from 1 to 20. For example, M can be between 1 to 5 in baseband sampling. N depends on the number of ultrasound beams associated with the transducer array, aperture(s), and/or subaperture(s). In some embodiments, N can be between 1 to 10. In some embodiments, N can be between 1 to 5 for IVUS imaging.

In some embodiments, identifying the at least one subaperture can include calculating signal responses at a given depth using a plurality of subapertures, and comparing the signal responses generated by each subaperture. For example, referring again to FIG. 8, the processing system can calculate the signal response for a given pixel or depth using the first subaperture 312, the second subaperture 314, and the third subaperture 316. The subaperture that yields the minimum signal response can be selected to for each pixel, and the identified minimum signal responses can be assembled or arranged into a minimized image. This process is repeated for each pixel in the image to generate the minimized image.

In other embodiments, the processing system can determine which of the subapertures yield a signal response below a threshold, and then average the signal responses yielded by those subapertures in order to determine the reduced or minimized response. In yet another embodiment, the processing system can determine which subapertures yield a signal response below a threshold, and then determine the variance of the signal responses produced by the below-threshold subapertures and determine the variances of those subapertures. In such embodiments, an upper bound signal response is determined based on the determined variance and average of the signal response using a programmable multiplier K. For example, upper bound=average+(K×variance of signal response of below-threshold subapertures). Where no subaperture yields a signal response below the threshold value, the threshold could be simply set to the determined upper bound. To account for the possibility of the upper bound being larger than the preselected threshold, the threshold could be set by finding the minimum of: the preselected threshold, the average signal response of subapertures yielding below-threshold signal responses, and the upper bound based on the average signal response, variance, and K. K can be any value determined to be appropriate for producing a reduced or minimized signal response. In some embodiments, K is defined based on a confidence level of 95% and a reliability of greater than 95%. The threshold used to identify subapertures for averaging could be, for example, 5% to 10% of the full aperture signal value. In another embodiment, the threshold could be selected or determined based on a desired dB value. For example, if it is desired to identify subapertures for minimized or reduced signal values falling below 40 dB, the threshold could be set to $10^{(-40\ dB/20)}$.

Figure 9:
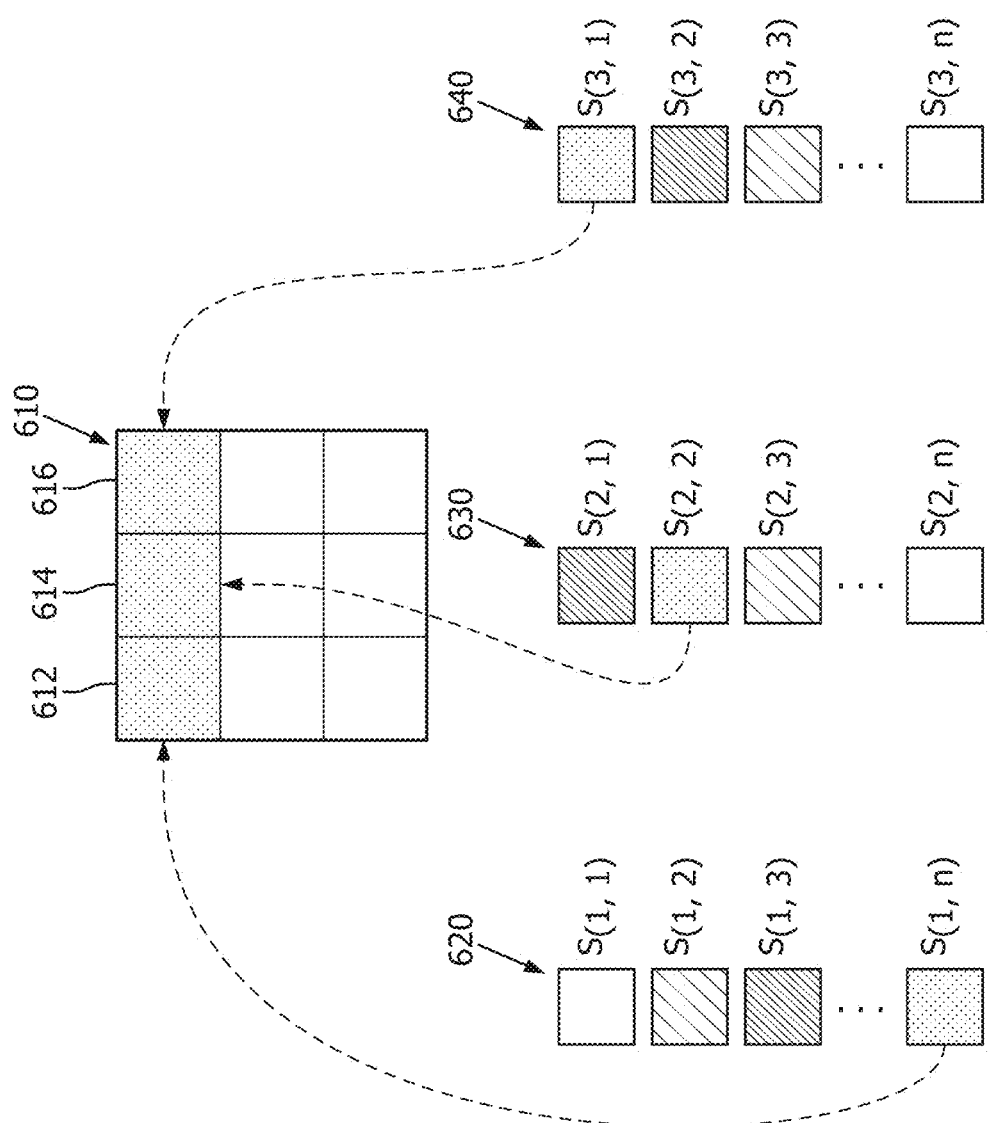
FIG. 9 is a diagrammatic graphical view of a procedure for generating a minimized image by identifying subapertures corresponding to reduced signal values, according to aspects of the present disclosure.

FIG. 9 illustrates the process of compiling the minimized image 610 using the determined minimum signal responses $S_{(m,n)}$ for each pixel. Regarding the nomenclature of the signal responses $S_{(m,n)}$, the first value "m" in the subscript denotes the corresponding pixel of the image 610, and the second value "n" in the subscript denotes the subaperture used to generate the signal response. Column 620 shows the signal responses associated with a first pixel 612 of the image 610, such that the first value in the subscript is 1 (e.g., $S_{(1,1)}$, $S_{(1,2)}$). Each signal response is represented by a particular shade, where lighter shades correspond to stronger signal responses, and darker shades correspond to weaker signal responses. Each column includes n signal response values corresponding to n different subapertures that are compared to determine the minimum signal response. From column 620, which includes signal response values corresponding to a first pixel 612, signal response $S_{(1,n)}$ exhibits the minimum signal response, as illustrated by the dark shade. Thus, signal response $S_{(1,n)}$ is selected as the signal response value for pixel 612 of the minimized image. Signals $S_{(1,1)}$, $S_{(1,2)}$, and $S_{(1,3)}$, have relatively higher signal response values, and thus are not selected for the minimized image. The relatively stronger signal responses yielded by subapertures corresponding to signal responses $S_{(1,1)}$, $S_{(1,2)}$, and $S_{(1,3)}$, may be the result of grating lobes in the corresponding pixel/depth of the full aperture image.

For the second pixel 614 of the minimized image 610, signal response $S_{(2,2)}$ is identified as the minimum signal response from column 630, and signal response $S_{(3,1)}$ is identified as the minimum signal response from column 640, corresponding to pixel 616. This process is repeated for all pixels in the image to produce the minimized image 610.

In some embodiments, the processing system outputs the minimized image to the display. However, it may be desirable to instead use the minimized image to generate a weighting mask, and apply the weighting mask to the original full aperture image to produce a grating lobe minimized image. For example, because the minimized image was created using smaller groups of transmit-receive pairs (i.e., subapertures instead of apertures), image resolution may be adversely affected in the minimized image. Furthermore, different subapertures may not share the same k-space, which can cause the point-spread function (psf) to vary across the minimized image. Further still, the minimized image created by identifying the minimum subapertures may introduce new artefacts or distortions to the minimized image. Accordingly, in step 540, the processing system generates a weighting mask based on the minimized image created in step 530. Generating the weighting mask can include applying spatial low-pass filters and/or median filters to the full aperture image created in step 520 and the minimized image created in step 530, and calculating a pixel-by-pixel ratio of the low-pass-filtered/median-filtered minimized image to the low-pass-filtered/median-filtered full aperture image. Then, a pixel-by-pixel minimum can be determined between 1 and the calculated ratio. For example, when a low-pass filter is used, the weighting mask can be generated according to the following relationship:

$$w = \min\left(1, \frac{LPF(I_{min})}{LPF(I_{full})}\right)$$

Where w is the weighting mask weighting value, $I_{min}$ is the minimized image, and $I_{full}$ is the full aperture image. It will be understood that the weighting mask yields values equal to or less than one. Thus, even when the low-pass-filtered minimized image signal is relatively greater than that of the low-pass-filtered full aperture image for a given pixel, the weighting mask will not increase the signal value for any given pixel. However, in other embodiments, the weighting mask may simply be generated by calculating, for each pixel or group of pixels, a ratio of the filtered minimized image to the filtered full aperture image.

Figure 10A:
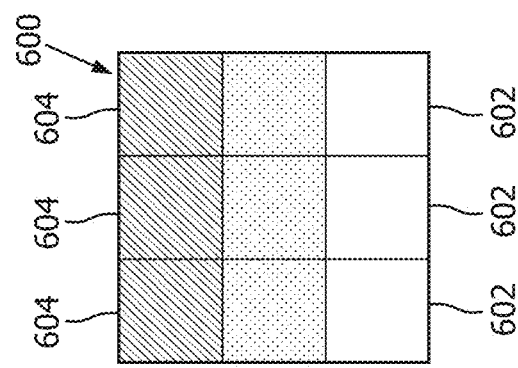
FIGS. 10A, 10B and 10C are diagrammatic views of a full aperture image, a weighting mask, and a grating lobe minimized image, respectively, according to aspects of the present disclosure.
Figure 10B:
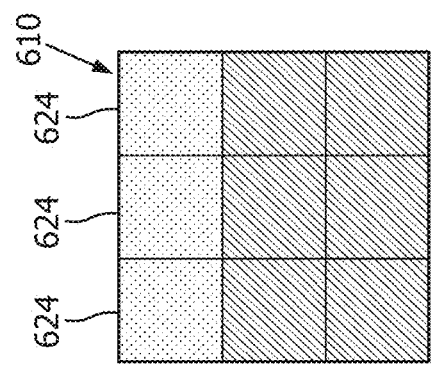
Figure 10C:
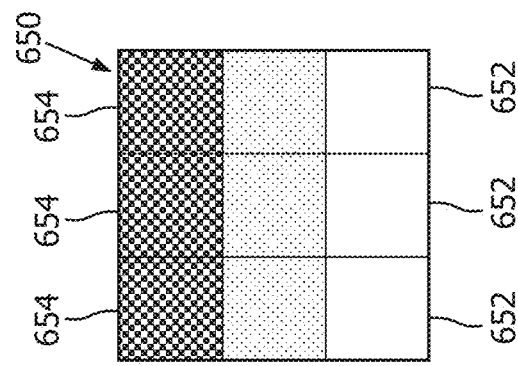

Referring again to FIG. 7, in step 550, the weighting mask w generated in step 540 is applied to the full aperture image $I_{full}$ to produce a grating lobe minimized image. This process is illustrated in FIGS. 10A, 10B, and 10C. FIG. 10A shows a full aperture image that includes a first set of pixels 602 representative of a true target, and a second set of pixels 604 associated with a grating lobe artefact. FIG. 10B shows a weighting mask 610 generated from a minimized image and a full aperture image according to the relationship described above. Each pixel of the weighting mask is associated with a weighting factor or weighting value ranging from zero to one that will be applied to a corresponding pixel of the full aperture image 600. The weighting mask 610 includes a dark set of pixels 624 corresponding to low weighting values. In that regard, because the minimized image signal values in the minimized image that correspond to the signal values of the full aperture image 600 are significantly lower than the signal values for the corresponding first set of pixels 604, the weighting mask 610 applies a weighting factor of less than 1 to the first set of pixels 604. This relatively low weighting factor is represented by the dark shade of the pixels 624. By contrast, the signal response values of the remaining pixels of the weighting mask 610 may not vary significantly from the corresponding signal response values of the full aperture image 600. Thus, the weighting factors of the remaining portions of the weighting mask 610 may be closer to 1, represented by a relatively lighter shade.

Referring now to FIGS. 7 and 10C, in step 560, a grating lobe minimized image 650 is generated based on the weighting mask 610 and the full aperture image 600, wherein the weighting mask 610 is based on the full aperture 600 image and the minimized image generated in step 530. Applying the weighting mask 610 to the full aperture image 600 can include a pixel-by-pixel multiplication or product of the weighting factor and corresponding image pixel in the image 600, where the image 600 is in linear magnitude form. In other embodiments, applying the weighting mask 610 can include subtracting the mask from a log magnitude version of the image 600. Furthermore, generating the grating lobe minimized image 650 can include using a log compression of the weighted image produced by the application of the weighting mask 610 to the full aperture image 600. Applying the weighting mask 610 to the image 600 can occur before or after scan conversion of the image. More generally, applying the weighting mask 610 for any given pixel may be any suitably chosen function of the full aperture image and the minimum intensity image. FIG. 10C shows a grating lobe minimized image 650 generated by applying the weighting mask 610 to the full aperture image 600 and using a log compression of the weighted image. The grating lobe minimized image 650 includes a first set of pixels 654 that corresponds to the first set of pixels 604 of the full aperture image 600. The weighted signal values of the first set of pixels 654 are significantly lower than the signal values of the second set of pixels 604 from the full aperture image 600, due to the effect of the weighting mask 610 on the second set of pixels 604. Accordingly, the presence and/or intensity of the grating lobe artefacts in the second set of pixels 604 is significantly reduced or eliminated, while the signal values associated with the true target remain the same, or relatively similar in the grating lobe minimized image 650.

Figure 11A:
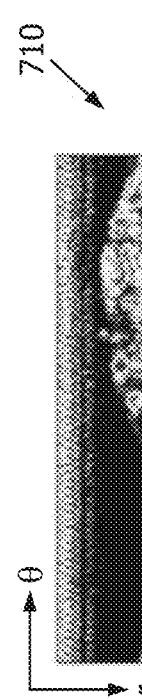
FIGS. 11A, 11B, 11C and 11D are ultrasound images at various stages in a grating lobe minimizing procedure, according to aspects of the present disclosure.

FIGS. 11A-11D illustrate an ultrasound image 700 being modified by the process 500 described above. FIG. 11A shows an original full aperture image 700 of an IVUS image presented in an r, θ format (e.g., a pre-scan-converted IVUS image). The image 700 shows a cross-sectional view of a vessel wall and a plurality of stent struts inside the vessel wall. In addition, the white arrows point to grating lobe artefacts, which may be caused in part by the stent struts, which can cause strong off-axis reflections of ultrasound energy. These grating lobe artefacts add clutter to the image 700 and make assessment of the vessel structure and/or stent struts difficult. Accordingly, the image 700 is processed according to the method 500 described above.

Figure 11C:
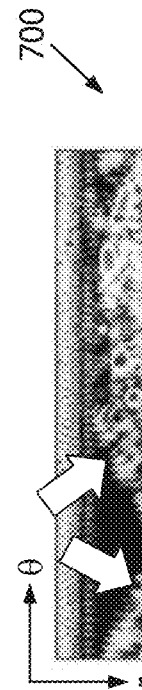
Figure 11B:
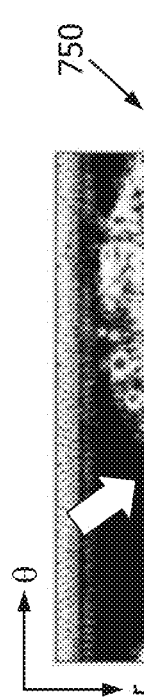
Figure 11D:

FIG. 11B shows a minimized image 710 generated according to step 530. In the minimized image 710, the presence or intensity of the grating lobe artefacts is significantly reduced. However, the minimized image 710 can include undesirable changes to the full aperture image 700, which can result in lost or distorted image details. Thus, a weighting mask 720 is produced according to step 540, which is shown in FIG. 11C. Each pixel of the weighting mask 720 can correspond to a weighting factor ranging from 0 to 1, where weighting factors closer to 0 are generally shown as darker, and weighting factors closer to 1 are shown as lighter. An area corresponding to the grating lobe artefacts of the original image 700 includes relatively darker shades, which correspond to lower weighting factors. These dark areas arise because the difference in signal response values between the pixels of the full aperture image and the pixels of the minimized image is relatively large. Finally, the weighting mask 720 is applied to the full aperture image 700 to produce a grating lobe minimized image 750, which is shown in FIG. 11D. The grating lobe minimized image 750 includes similar or identical image features as FIG. 11A, but with the grating lobe artefacts reduced or eliminated.

Figure 12B:
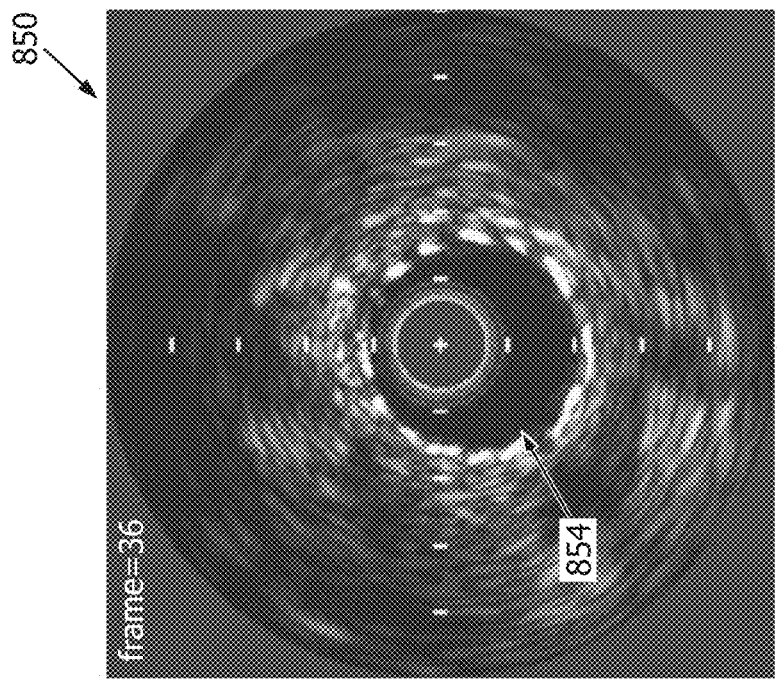
FIG. 12B is a grating lobe minimized IVUS image generated from the full aperture IVUS image shown in FIG. 12A, according to aspects of the present disclosure.
Figure 12A:
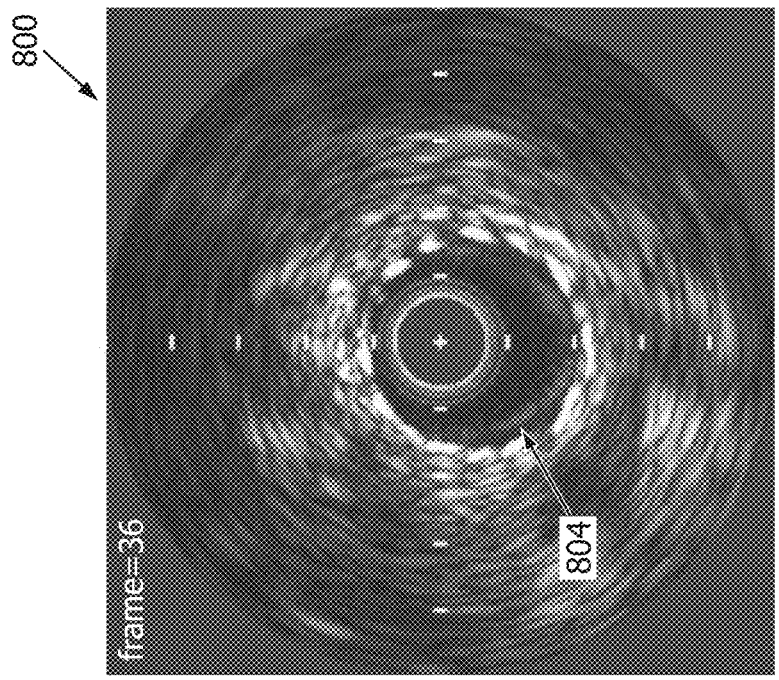
FIG. 12A is a full aperture IVUS image of a vessel and a stent, according to aspects of the present disclosure.

FIGS. 12A and 12B show a full aperture IVUS 800 image and a grating lobe minimized IVUS 850 image, respectively. The full aperture IVUS image 800 is a cross-sectional view of a blood vessel including a stent. The full aperture image 800 also shows grating lobe artefacts 804, which may be caused, in part, by off-axis reflections from the stent struts. FIG. 12B shows a grating lobe minimized image 850 generated from the full aperture image 800 using a minimum subaperture process. In contrast to the full aperture image 800, the area 854 of the grating lobe minimized image 850, which corresponds to the area in which the grating lobe artefacts 804 are located in the full aperture image 800, does not include grating lobe artefacts. However, the grating lobe minimized image 850 includes all or a substantial portion of the remaining image features of the original full aperture image 800, such as the stent, vessel structure, tissue speckle pattern, etc.

It will be understood that one or more of the steps of the method, such as activating the scan sequence, generating the full aperture image, the minimized image, the weighting mask, and the grating lobe minimized image, and outputting the grating lobe minimized image to the display, can be performed by one or more components of an ultrasound imaging system, such as the processor, a multiplexer, a beamformer, a signal processing unit, an image processing unit, or any other suitable component of the system. For example, activating the scan sequence may be carried out by a processor in communication with a multiplexer configured to select or activate one or more elements of an ultrasound transducer array. In some embodiments, generating the ultrasound images may include beamforming incoming signals from the ultrasound imaging device and processing the beamformed signals by an image processor. The processing components of the system can be integrated within the ultrasound imaging device, contained within an external console, or may be a separate component.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system comprising:
   an array of acoustic elements configured to transmit ultrasound energy into an anatomy and to receive ultrasound echoes associated with the anatomy; and
   a processor in communication with the array and configured to:
      control the array to activate a plurality of apertures in a scan sequence, each aperture of the plurality of apertures comprising a plurality of subapertures associated with one or more acoustic elements of the array;
      generate a full aperture image comprising a plurality of pixels, wherein each pixel is associated with signal values acquired by an aperture of the plurality of apertures;
      identify, for one or more pixels of the full aperture image, at least one subaperture of the aperture that acquired the signal values, wherein the at least one subaperture corresponds to a reduced signal value for the one or more pixels;
      generate a minimized image based on the identified at least one subaperture for the one or more pixels; and
      output, to a display in communication with the processor, a grating lobe minimized image based on the full aperture image and the minimized image.

2. The ultrasound imaging system of claim 1, wherein the processor is configured to identify, for the one or more pixels of the full aperture image, a single subaperture of the plurality of subapertures corresponding to a minimum signal value for the one or more pixels.

3. The ultrasound imaging system of claim 1, wherein the processor is further configured to:
   generate a weighting mask based on the minimized image and the full aperture image; and
   apply the weighting mask to the full aperture image to generate a weighted image.

4. The ultrasound imaging system of claim 3, wherein the processor generating the weighting mask includes calculating a pixel-by-pixel ratio of a filtered minimized image and a filtered full aperture image.

5. The ultrasound imaging system of claim 4, wherein the filtered minimized image comprises at least one of a low-pass-filtered minimized image or a median-filtered minimized image, and wherein the filtered full aperture image comprises at least one of a low-pass-filtered full aperture image or a median-filtered full aperture image.

6. The ultrasound imaging system of claim 3, wherein the processor is configured to generate the grating lobe minimized image, wherein the processor generating the grating lobe minimized image includes a log compression of the weighted image.

7. The ultrasound imaging system of claim 1, wherein each aperture spans N transmit elements and N receive elements of the array, wherein each subaperture spans M transmit elements and M receive elements of the array, and wherein M is less than N.

8. The ultrasound imaging system of claim 7, wherein each subaperture is associated with a contiguous portion of the acoustic elements of a corresponding aperture.

9. The ultrasound imaging system of claim 1, further comprising an intravascular ultrasound (IVUS) catheter, and wherein the array is positioned around a distal portion of the IVUS catheter.

10. A method for ultrasound imaging, comprising:
    activating, by a processor in communication with an array of acoustic elements, a plurality of apertures in a scan sequence, each aperture of the plurality of apertures associated with a scan line and comprising a plurality of subapertures associated with one or more acoustic elements of the array;
    generating a full aperture image comprising a plurality of scan lines that include signal values over a range of depths acquired by an aperture of the plurality of apertures;
    comparing, at one or more depths of the range of depths, at least a portion of the signal values corresponding to one or more subapertures of the aperture that acquired the signal values;
    determining, based on the comparing, at least one subaperture of the aperture that acquired the signal values, wherein the at least one subaperture corresponds to a reduced signal value for the one or more depths;
    generating a minimized image based on the reduced signal value; and
    outputting, to a display in communication with the processor, a grating lobe minimized image based on the full aperture image and the minimized image.

11. The method of claim 10, wherein determining the reduced signal value for the one or more depths comprises identifying a single subaperture, for each depth, that corresponds to a minimum signal value.

12. The method of claim 10, further comprising:
    generating a weighting mask based on the minimized image and the full aperture image; and
    applying the weighting mask to the full aperture image to generate a weighted image.

13. The method of claim 12, wherein generating the weighting mask includes calculating a pixel-by-pixel ratio of a filtered minimized image and a filtered full aperture image.

14. The method of claim 13, wherein the filtered minimized image comprises at least one of a low-pass-filtered minimized image or a median-filtered minimized image, and wherein the filtered full aperture image comprises at least one of a low-pass-filtered full aperture image or a median-filtered full aperture image.

15. The method of claim 12, further comprising generating, by the processor, the grating lobe minimized image by a log compression of the weighted image.

16. The method of claim 10, wherein each aperture spans N transmit elements and N receive elements of the array, wherein each subaperture spans M transmit elements and M receive elements of the array, and wherein M is less than N.

17. The method of claim 16, wherein each subaperture is associated with a contiguous portion of the acoustic elements of a corresponding aperture.

18. The method of claim 10, wherein activating the plurality of apertures of the array comprises activating a plurality of apertures of an array positioned around a distal portion of an intravascular ultrasound (IVUS) catheter.

19. An ultrasound imaging system, comprising:
  an array of acoustic elements configured to transmit ultrasound energy into an anatomy and to receive ultrasound echoes associated with the anatomy; and
  a processor in communication with the array and configured to:
    activate a plurality of apertures in a scan sequence, each aperture of the plurality of apertures comprising a plurality of subapertures associated with one or more acoustic elements of the array;
    generate a full aperture image comprising a plurality of pixels, wherein each pixel is associated with signal values acquired by an aperture of the plurality of apertures;
    generate a reduced image comprising a plurality of reduced signal pixels, wherein generating the plurality of reduced signal pixels comprises:
      comparing at least a portion of the signal values corresponding to one or more subapertures associated with a corresponding pixel or group of pixels; and
      identifying, based on the comparing, at least one subaperture of the aperture that acquired the signal values, wherein the at least one subaperture corresponds to a reduced signal value for the corresponding pixel or group of pixels; and
    output, to a display in communication with the processor, a grating lobe minimized image based on the full aperture image and the reduced image.

* * * * *